United States Patent
Lee et al.

(10) Patent No.: US 8,624,008 B2
(45) Date of Patent: Jan. 7, 2014

(54) APTAMER AND DETECTION METHOD FOR C-REACTIVE PROTEIN

(75) Inventors: Gwo-Bin Lee, Tainan (TW); Shu-Chu Shiesh, Tainan (TW); Chao-June Huang, Taipei (TW); Hsin-I Lin, Tainan County (TW)

(73) Assignee: National Cheng-Kung University, Tainan (TW)

( * ) Notice: Subject to any disclaimer, the term of this patent is extended or adjusted under 35 U.S.C. 154(b) by 436 days.

(21) Appl. No.: 12/924,225

(22) Filed: Sep. 22, 2010

(65) Prior Publication Data

US 2011/0318846 A1   Dec. 29, 2011

(30) Foreign Application Priority Data

Jun. 25, 2010 (TW) .............................. 99120849 A

(51) Int. Cl.
    *C07H 21/02* (2006.01)
(52) U.S. Cl.
    USPC ...................................................... 536/23.1
(58) Field of Classification Search
    USPC ...................................................... 536/23.1
    See application file for complete search history.

(56) References Cited

U.S. PATENT DOCUMENTS

| | | | |
|---|---|---|---|
| 2006/0110739 | A1 | 5/2006 | Heyduk et al. |
| 2008/0044834 | A1 | 2/2008 | Heyduk |
| 2008/0171322 | A1 | 7/2008 | Heyduk et al. |
| 2009/0196938 | A1 | 8/2009 | Vogt |
| 2009/0202520 | A1 | 8/2009 | Lupher, Jr. et al. |
| 2009/0202990 | A1 | 8/2009 | Heyduk et al. |

FOREIGN PATENT DOCUMENTS

| | | |
|---|---|---|
| TW | I230257 | 4/2005 |
| TW | I249031 | 2/2006 |
| TW | I251079 | 3/2006 |
| TW | 200812626 | 3/2008 |
| TW | 200812627 | 3/2008 |
| TW | 200912282 | 3/2009 |
| TW | 200912310 | 3/2009 |
| WO | WO 9319087 A1 * | 9/1993 |

OTHER PUBLICATIONS

Pestourie et al. (Biochemie 2005; 87:921-930).*
Ulrich et al. (Braz J Med Biol Res 2001; 34:295-300).*
A. Bini, et al., "Development of an optical RNA-based aptasensor for C-reactive protein" Analytical and Bioanalytical Chemistry (2008), vol. 390, pp. 1077-1086.
John G. Bruno et al., "Preliminary development of DNA aptamer-Fc conjugate opsonins" Journal of Biomedical Materials Research, vol. 90A, Issue 4, pp. 1152-1161, Sep. 15, 2009, Published online Jul. 31, 2008 in Wiley InterScience (www.interscience.wiley.com).
Sonia Centi et al., "Detection of C Reactive Protein (CRP) in Serum by an Electrochemical Aptamer-Based Sandwich Assay" Electroanalysis (2009), vol. 21, No. 11, pp. 1309-1315.

(Continued)

*Primary Examiner* — Jon E Angell
(74) *Attorney, Agent, or Firm* — J.C. Patents

(57) ABSTRACT

An aptamer specifically binding to C-reactive protein (CRP) is provided. The aptamer includes a following nucleotide sequence: 5'-angngggngnntgnnt-3', wherein n is a nucleotide selected from a, t, c and g.

8 Claims, 5 Drawing Sheets

(56) References Cited

OTHER PUBLICATIONS

Johanna Pultar et al., "Aptamer-antibody on-chip sandwich immunossay for detection of CRP in spiked serum" Biosensors and Bioelectronics, vol. 24 (2009), pp. 1456-1461.

Jianlong Wang et al., "Aptamer-Au NPs conjugates-enhanced SPR sensing for the ultrasensitive sandwich immunoassay" Biosensors and Bioelectronics, vol. 25 (2009), pp. 124-129.

Yi-Ning Yang et al., "An integrated microfluidic system for C-reactive protein measurement" Biosensors and Bioelectronics, vol. 24 (2009), pp. 3091-3096.

Huang et al, "Integrated microfluidic system for rapid screening of CRP aptamers utilizing systematic evolution of ligands by exponential enrichment (SELEX)," Biosensors and Bioelectronics, Dec. 28, 2009, pp. 1761-1766, vol. 25, No. 7.

* cited by examiner

APTAMER AND DETECTION METHOD FOR C-REACTIVE PROTEIN

CROSS-REFERENCE TO RELATED APPLICATION

This application claims the priority benefit of Taiwan application serial no. 99120849, filed on Jun. 25, 2010. The entirety of the above-mentioned patent application is hereby incorporated by reference herein and made a part of this specification.

BACKGROUND OF THE INVENTION

1. Field of the Invention

The invention is directed to an aptamer and a detection method. More particularly, the invention is directed to an aptamer and a detection method relating to C-reactive protein.

2. Description of Related Art

C-reactive proteins (CRPs) are proteins synthesized by the liver and present in plasma. Being a member of the pentraxin family, CRPs have pentagon ring structures constituted by five identical subunits that are non-covalently bonded. Here, each of the subunits includes 224 amino acids and has a molecular weight of approximately 25 kilo-Dalton (kDa). CRPs are mainly synthesized by liver cells reactive to cytokines, and the half-life thereof in plasma is about 18-20 hour (hr).

Clinically, CRPs are an index for human inflammation reactions and valuable for the screening and monitoring of tissue damages. In general, the concentration of CRPs in human body is very low, less than 10 milligram/liter (mg/L), and is maintained stable for a long period before new stimuli occur. However, in the occurrence of acute inflammation such as external wound, virus infection, myocardial infraction and so on, the synthesis of CRPs increases rapidly in 4-6, hr, and reaches its peak at 36-50 hr, so that the concentration of CRPs in the body is increased to more than 100-1000 times of its normal value. The range of increase in the CRP concentration is usually positively correlated to the level of infection. Consequently, the concentration of CRPs is reduced to normal concentration rapidly after suitable treatment.

Since the concentration of CRPs rapidly increases during inflammation, methods with lower sensitivity, such as nephelometry, are usually adopted clinically to determine inflammation symptoms related to CRP concentration. Here, nephelometry has the limit of detection of about 5 mg/L. Nevertheless, many recent studies show that the concentration of CRPs in human plasma may be positively correlated to the occurrence of cardiovascular disease. The American Heart Association (AHA) and the Center for Disease Control and Prevention (CDC) also define the relationship between CRP concentration and cardiovascular disease. People with the CRP concentration lower than 1.0 mg/L have low risks, people with the CRP concentration ranging from 1.0 to 3.0 mg/L have medium risks, and people with the CRP concentration higher than 3.0 mg/L have high risks. Here, people with high risks have double the chance of getting cardiovascular disease than people with low risks. On the other hand, as slight inflammation occurs in the hardening of the arteries, some studies also show the CRP concentration to be the predictive index of arteriosclerosis. Thus, methods including high sensitivity CRP (Hs-CRP) detection method and enzyme linked immunoassay (ELISA) have been clinically adopted for detecting CRPs with low concentration, and the detected results are then applied in assessment and prediction of cardiovascular disease.

In other words, the qualitative analysis and the quantitative analysis of CRPs play major roles in the diagnosis and prevention of diseases. For ELISA method, the high sensitivity comes from the specific bonding between antigens and antibodies. However, the antibodies used in the detection method have disadvantages such as large variation, easily influenced by environment, difficult preservation, and potential contamination of organisms. Hence, the clinical application of the detection for CRPs is limited and cannot be widely used for the assessment and prevention of diseases.

SUMMARY OF THE INVENTION

The invention is directed to an aptamer specifically binding to a C-reactive protein (CRP).

The invention is further directed to a detection method of a CRP, where the detection method is highly sensitive.

The invention is directed to an aptamer specifically binding to a CRP and including a following nucleotide sequence: 5'-angngggngnntgnnt-3' (SEQ ID NO: 1). Herein, n is a nucleotide selected from a, t, c, and g.

In one embodiment of the invention, the aptamer includes a following nucleotide sequence: 5'-atgggggggtatgatt-3' (SEQ ID NO: 2).

In one embodiment of the invention, the aptamer includes a following nucleotide sequence: 5'-aagcgggtgggtgtgt-3' (SEQ ID NO: 3).

In one embodiment of the invention, a binding affinity (Kd) between the aptamer and the CRP ranges from 0.3 nanomole (nM) to 30 nM.

In one embodiment of the invention, the aptamer has a 5' end modified by a thiol group, a biotin, a fluorescent label, or an enzyme.

In one embodiment of the invention, the aptamer includes 10 to 80 nucleotides.

The invention is further directed to a detection method for a CRP. The detection method is suitable for detecting the CRP in a sample, and includes the following. An aptamer as aforementioned is provided. The sample and the aptamer are mixed, such that the CRP in the sample and the aptamer bind to form a C-reactive protein-aptamer. The CRP or the aptamer in the CRP-aptamer is then detected.

In one embodiment of the invention, the aptamer is labeled with a fluorescent label or a luminescent label.

The invention is directed to another detection method for the CRP. The detection method is suitable for detecting the CRP in a sample, and includes the following. A plurality of beads is provided, and the beads have been non-covalently bonded with aptamers aforementioned. The beads and the sample are mixed, such that the aptamers on the beads bind with the C-reactive proteins in the sample. C-reactive protein antibodies are then added to the sample mixed with the beads, such that the C-reactive protein antibodies bind with the C-reactive proteins bound on the beads. The unbound C-reactive protein antibodies are removed. The C-reactive protein antibodies bound to the beads through the C-reactive proteins are detected.

In one embodiment of the invention, the aptamers and the beads are non-covalently bonded through a biotin-streptavidin interaction.

In light of the foregoing, the aptamer of the invention is capable of specifically binding to the CRP, and the detection method for the CRP adopting the aptamer thus has high sensitivity.

In order to make the aforementioned and other features and advantages of the invention more comprehensible, several embodiments accompanied with figures are described in detail below.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DESCRIPTION OF EMBODIMENTS

Figure 1:
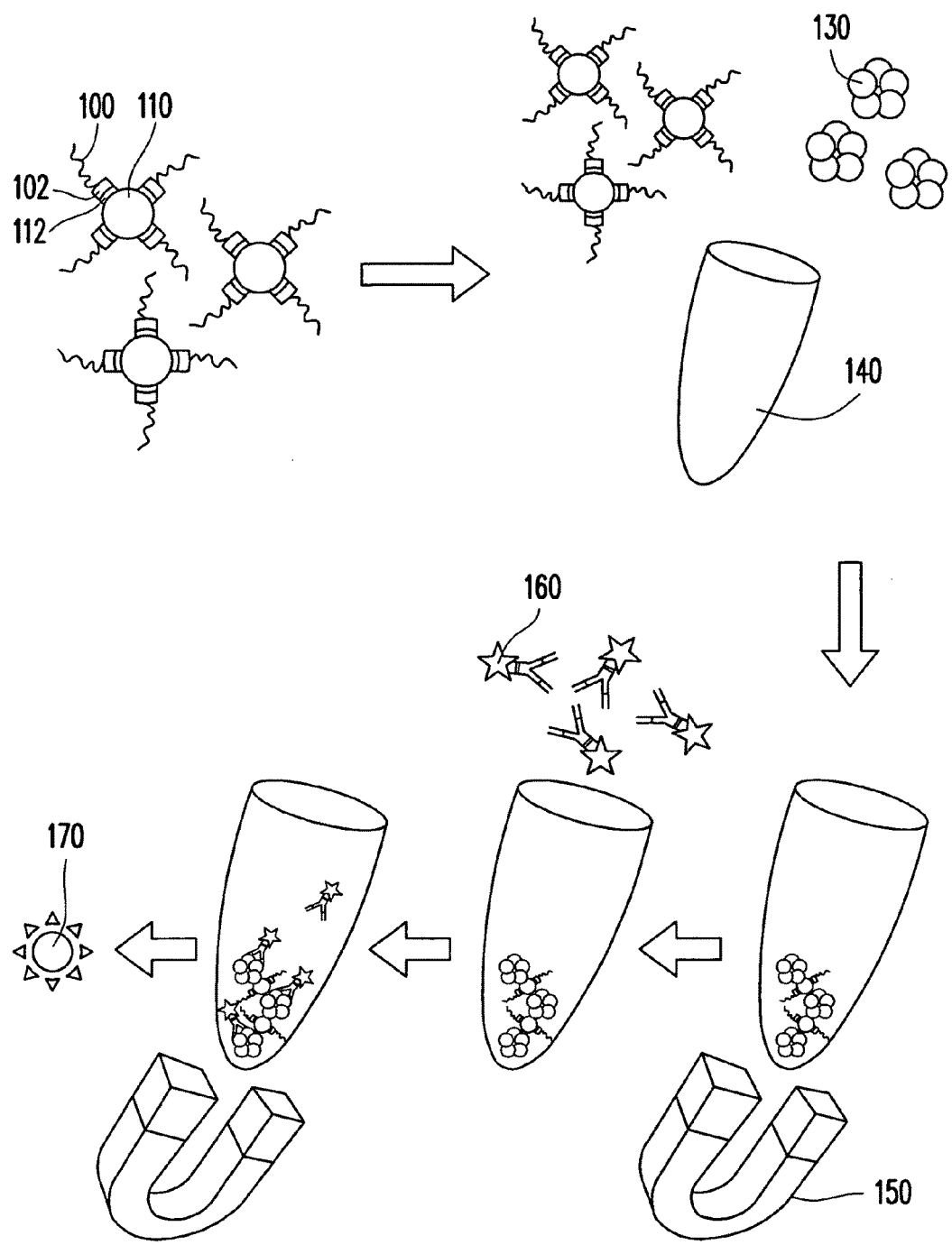
FIG. 1 shows a schematic flow chart of a detection method for a C-reactive protein (CRP) according to an embodiment of the invention.

The invention is directed to an aptamer specifically binding to a C-reactive protein (CRP). The sequence listings disclosed in the content of the disclosure are compiled in the "SEQUENCE LISTING" section. The aptamer includes a following nucleotide sequence: 5'-angngggngnnntgnnt-3' (SEQ ID NO: 1). Herein, n is a nucleotide selected from adenine (a), thymine (t), cytosine (c), and guanine (g). In other words, the aptamer is a single strand of deoxyribonucleic acid (DNA) fragment and at least includes the sequence of 5'-angngggngnnntgnnt-3' (SEQ ID NO: 1) for binding specifically with the CRP. In one embodiment, a total length of the aptamer includes 10 to 80 nucleotides. In one embodiment, the aptamer includes a sequence of 5'-atggggggtatgatt-3' (SEQ ID NO: 2), and an entire sequence of the aptamer is 5'-ggcaggaagacaaacac-gatgggggggtatgatttgatgtggttgttgcatgatcgtggtctgtggtgctgt-3' (SEQ ID NO: 4), which includes 72 nucleotides in total. In another embodiment, the aptamer includes a sequence of 5'-aagcgggtgggtgtgt-3' (SEQ ID NO: 3), and an entire sequence of the aptamer is 5'-ggcaggaagacaaacaca-caagcgggtgggtgtgtactattgcagtatctattctgtggtctgtggtgctgt-3' (SEQ ID NO: 5), which includes 72 nucleotides in total.

The aptamer of the invention is capable of specifically binding to the CRP and a binding affinity (Kd) between the aptamer and the CRP ranges from 0.3 nanomole (nM) to 30 nM, for example. In one embodiment, the binding affinity (Kd) between the aptamer and the CRP is, for example, 3.51 nM. In other words, the aptamer and the CRP have high affinity and high specificity therebetween. The aptamer of the invention is thus suitable for detecting the CRP. In particular, since the aptamer of the invention is fabricated through chemical synthesis, for example, the aptamer has the following advantages comparing to antibodies: does not require fabrication in cells or animals, and the fabrication is thus simple, cheap, and has minimal batch difference; the targets can be toxins or molecules lacking immune source, and are not affected by the toxicity tolerance and immune ability of the organism itself; and not easily influenced by environmental factors such as external temperature, humidity, and the like, and can be stored long-term. In addition, in one embodiment, a 5' end of the aptamer can be modified by a thiol group, a biotin, a fluorescent label, a luminescent label, an enzyme, or other substances, so that the 5' end can bind with specific substrates or have labeling characteristics such as light emission. Here, the fluorescent label includes chemical substances such as fluorescein isothiocyanate (FITC), Cy3, and Cy5, the luminescent label includes chemical compounds such as acridinium esters, and enzymes includes alkaline phosphatase, horse radish perioxidase (HRP), and the like.

It should be noted that other than adopting the aptamer of the invention for detecting the CRP, the high affinity and high specificity between the aptamer and the CRP can also be applied in other biotechnologies. For example, the aptamer can be adopted as a target drug for carrying drugs or directly approaching a site with high expression of the CRP to bind with the CRP, so as to release drugs or inhibit the expression of the CRP directly, thereby treating or preventing diseases related to the expression of the CRP. Obviously, other than applying the aptamer for detection or as the target drug, persons of common knowledge in the art should understand that the aptamer of the invention is also suitable for other biotechnologies relying on the high affinity and high specificity of the CRP, and the details are thus not illustrated herein.

The invention is further directed to a detection method for a CRP. The detection method is suitable for detecting the CRP in a sample, and includes the following. An aptamer of the invention is provided. The sample and the aptamer are mixed, such that the CRP in the sample and the aptamer bind to form a C-reactive protein-aptamer. The CRP or the aptamer in the CRP-aptamer is then detected. In an embodiment, the detection method for the CRP is an enzyme linked immunoassay (ELISA) method (including a sandwich ELISA method), a surface plasmon resonance (SPR) bio-sensing method, and so on. Moreover, the detection method for the CRP can reach much higher sensitivity than the conventional detection methods for the CRP and increase the stability and convenience of these conventional detection methods. In other words, in one embodiment, since the aptamer can be used to replace the CRP antibody, the detection method for the CRP in the invention can be any detection method adopting the binding principle of the CRP antibody and antigen.

In an embodiment, the detection method for the CRP is, for example, an ELISA method, which includes the following, for example. Aptamers of the invention are coated on a plastic tray having wells, and excessive aptamers are washed off. In this step, the aptamers are conjugated on plastic tray by, for instance, modifying the streptavidin or the sulfhydryl group. A sample to be tested is added. Here, if the sample includes the CRPs, the CRPs in the sample then bind the aptamers on the plastic tray having wells. Next, the plastic tray is washed off to remove the excessive sample, and antibodies carrying enzymes are added. Herein, the antibodies carrying the enzymes can form bonds with the CRPs. Later, the unbound antibodies are washed off, and enzyme substrates are added for the enzymes to elicit a color. The absorbency in the plastic tray is measured using a detecting machine, and the content of the colored final product is then evaluated for measuring the content of the CRPs in the sample to be tested. In the present embodiment, as the aptamers and the CRPs have high affinity and high specificity, the aptamers are capable of capturing the CRPs in the sample on the tray for facilitating the subsequent step of detecting the CRPs. In addition, being DNA fragments, the aptamers are not easily influenced by environmental factors such as external temperature, humidity, and the like. The detection method for the CRPs in the present embodiment therefore has high sensitivity, high stability, and high accuracy.

In an embodiment, the detection method for the CRP is, for example, the sandwich ELISA method, which includes the following, for example. Referring to FIG. 1, a 5' end of each of aptamers 100 is modified by a biotin 102, for example. The aptamers 100 and beads 110 modified with streptavidins 112 on the surface are non-covalently bonded, so that the aptamers 100 are connected to the beads 110. In this step, since the biotins 102 and the streptavidins 112 have high affinity therebetween, the aptamers 100 and the beads 110 can rapidly bond to form a plurality of aptamer-bead complexes, where the non-covalent bonds between the aptamers and the beads are not easily affected by pH, temperature, organic solvent, or denaturant. In other embodiments, the aptamers 100 and the beads 110 can also be bonded by bonding methods other than the biotin and the streptavidin, and the invention is not limited thereto. The beads 110 connected with the aptamers 100 and a series of diluted CRP standard solutions or samples are mixed in an eppendorf 140 to undergo bonding. In this step, since the aptamers 100 have high affinity and specificity toward CRPs 130, the aptamers 100 on the beads 110 bind with the CRPs 130 in the CRP standard solution or the sample to form CRP-aptamer-bead complexes. Thereafter, the beads 110 are adhered to a sidewall of the eppendorf 140 with an external magnetic field 150, and impurities not bound with the beads 110 are washed off with a washing solution. Next, CRP antibodies 160 labeled with a labeling substance such as luminescence or fluorescence is added. The CRP antibodies 160 not bonded with the beads 110 are washed off with the washing solution. Here, the luminescence is acridinium ester. In this step, the CRP antibodies 160 bind with the CRPs 130 bound to the beads 110. Next, a standard curve of the CRP standard solutions is established by detecting a luminescent intensity 170 of the CRP antibodies 160. A concentration of the CRPs in the sample is consequently calculated. In the present embodiment, as the aptamers 100 and the CRPs 130 have high affinity and high specificity therebetween, the aptamers 100 are capable of capturing the CRPs 130 in the sample on the beads 110 for facilitating the subsequent step of detecting the CRPs 130. In addition, each being a DNA fragment, the aptamers are not easily influenced by environmental factors such as external temperature, humidity, and the like. The detection method for the CRPs in the present embodiment therefore has high sensitivity, high stability, and high accuracy.

In an embodiment, a detection method for a CRP is, for example, a SPR bio-sensing method, which includes the following. Aptamers of the invention are coated on a metal thin film surface. Then, CRPs in a sample bind to the aptamers. In this step, the binding of the CRPs and the aptamers leads to a change in a resonance angle, such that the complete process of affinity reactions such as the binding and the dissociation between the aptamers and the CRPs in the sample can be obtained by detecting the change of the resonance angle. In the present embodiment, as the aptamers and the CRPs have high affinity and high specificity, the aptamers are capable of capturing and then binding with the CRPs in the sample, so as to detect the CRPs through the change of the resonance angle. In addition, each being a DNA fragment, the aptamers are not easily influenced by environmental factors such as external temperature, humidity, and the like. The detection method for the CRPs in the present embodiment therefore has high sensitivity, high stability, and high accuracy.

It should be noted that although in the embodiments aforementioned, the CRPs of the invention are applied in the ELISA method and the SPR bio-sensing method as examples, the detection method for the CRPs in the invention is not limited thereto. In other words, as the aptamers of the invention have high affinity and high specificity to the CRPs, the aptamers can be applied in any detection method for detecting the CRPs. Especially, as the aptamers of the invention can replace the CRP antibodies, the detection method for the CRP in the invention can be adopted in any detection method using binding principle of the CRP antibodies and the antigens. These methods should be well known to those skilled in the art and are not described in detail hereinafter.

In the following, several experiments are provided to illustrate a method for screening the aptamers of the invention, verify the high affinity and specificity of the aptamers toward the CRPs, and to depict practical applications of the detection method for the CRPs in the invention. The following illustrations are provided to describe the invention in detail for the implementation of persons skilled in the art, and not used to limit the scope of the invention.

Experiment 1

Initial Screening of Aptamers Having Affinity to CRPs

1. Establishment of Oligonucleotide Library

An oligonucleotide library includes $4^{40}$ types of oligonucleotides. These oligonucleotides are synthesized by Medclub Scientific Co. Ltd., Taiwan, and each has a 72-mer nucleotide sequence shown in a SEQ ID NO:6. The 72-mer nucleotide sequence includes a random sequence constituted by 40 nucleotides (represented by n), a 5'-primer region constituted by 16 nucleotides, and a 3'-primer region constituted by 16 nucleotides:

5'-ggcaggaagacanaca-[n]$_{40}$-tggtctgtggtgctgt-3' (SEQ ID NO: 6). Here, n represents a nucleotide selected from adenine (a), thymine (t), cytosine (c), and guanine (g). The 5'-primer region and the 3'-primer region are respectively designed to be nucleotide sequences recognized by Super-Therm Gold DNA polymerase (Bertec Enterprise Co. Ltd., Taiwan) for performing a polymerase chain reaction (PCR).

Then, a suitable amount of oligonucleotide library is dissolved in deionized water to obtain a 10 micro-mole (μM) oligonucleotide library stock solution for use.

2. Fabrication of CRP-Conjugated Beads

Dynabeads M-450 Epoxy (Cat. No. 140.11, Invitrogen, USA, concentration of 4×10$^8$ bead/milli-liter (mL)) in deionized water are diluted 20 times with phosphate buffered saline (PBS). Next, 100 micro-liter (μL) of the diluted Dynabeads M-450 Epoxy are extracted to an eppendorf using a pipette, and the eppendorf is placed in a magnet (Dynal MPC™, Invitrogen, USA), so that the Dynabeads M-450 Epoxy are attracted by the magnet so as to move toward the magnet and adhere to an inside wall of the eppendorf. Residues in the eppendorf not attracted by the magnetic field are removed. Subsequently, 100 μL of carbonate buffer (pH 9.7) and 20 micro-gram (μg) of CRP (in Tris buffer, which contains 10 milli-mole (mM) Tris, 50 mM NaCl, and 2 mM $CaCl_2$) are added to the eppendorf and mixed well. The eppendorf is then moved out from the magnet and placed under 4° C. for reaction overnight, so that the CRPs are conjugated to the Dynabeads M-450 Epoxy to form CRP-conjugated beads (referred as beads A).

Thereafter, the eppendorf is placed inside the magnet, such that the beads A are adsorbed to the inside wall of the eppendorf. Residues in the eppendorf that are not attracted by the magnetic field are removed and the beads A are washed three times with PBS. Afterwards, the eppendorf is moved out of the magnet and placed under 4° C. for blocking overnight with 1% bovine serum albumin (BSA). The beads A in the eppendorf are then washed three times with PBS. Finally, 200 μL of Tris buffer is added to the eppendorf to suspend the beads A sufficiently. Accordingly, a bead solution A with a concentration of $10^7$ bead/mL is obtained and stored under 4° C. for use.

3. Screening Aptamers Having Affinity to CRPs Using Integrated Microfluidic Chip System An integrated microfluidic chip system is provided. The integrated microfluidic chip system is assembled by a glass plate and two polydimethylsiloxane (PDMS) substrate. The integrated microfluidic chip system includes a reaction tank, a mixing/transporting unit located above the reaction tank, a waste liquid tank, a waste liquid channel configured to connect the waste liquid tank and the reaction tank, a washing solution storage tank for storing a washing buffer A (PBST, 0.01 M sodium phosphate buffer containing 155 mM NaCl and 0.2% of Tween 20, pH 7.4), a washing solution channel configured to connect the reaction tank and the washing solution storage tank, a washing solution mixing/transporting unit located above the washing solution storage tank and configured for transporting the washing solution to the washing solution channel, a reagent storage tank for the PCR reagent (as shown in Table 1), a reagent channel configured to connect the reaction tank and the reagent storage tank, a reagent mixing/transporting unit located above the reagent storage tank and configured for transporting the reagent to the reagent channel, a temperature control unit located below the reaction tank and configured to heat and sense the temperature of the reaction tank, and a magnetic field generating unit located below the reaction tank and configured to generate the magnetic field.

The oligonucleotide library stock solution (3 μL), the bead solution A (17 μL), and 1% BSA solution (20 μL) obtained from the aforementioned methods are added to the reaction tank of the integrated microfluidic chip system. The reaction is then mixed for five minute (min) using the mixing/transporting unit, so that the oligonucleotides having affinity to the CRPs bind to the CRPs on the beads A respectively so as to form different oligonucleotide-CPR-bead complexes. Afterwards, the magnetic field generating unit is turned on, and the oligonucleotide-CPR-bead complexes are affected by the magnetic field and thus adsorbed to the bottom of the reaction tank. Next, the washing solution mixing/transporting unit is activated, so that the washing buffer A in the washing solution storage tank is transported to the reaction tank through the washing solution channel. The washing solution mixing/transporting unit is re-activated, such that the oligonucleotides which do not have affinity to the CRPs and the remaining solution in the reaction tank flow to the waste liquid tank through the waste liquid channel. The magnetic field generating unit is turned off and the reagent mixing/transporting unit is activated, so that 30 μL of a solution having contents shown in Table 1, the PCR reagent dispensed according to the volume of the solution, and 12 μL of mineral oil flow into the reaction tank. The reagent mixing/transporting unit is turned off subsequently.

Thereafter, the temperature control unit is activated to adopt the oligonucleotides having affinity to the CRPs as templates. Moreover, a pair of forward primer F1 and reverse primer R1 with nucleotide sequences designed based on the nucleotide sequences in the 5'-primer region and the 3'-primer region respectively is used to perform the PCR reaction with reaction conditions shown in Table 1 so as to replicate DNA fragments with nucleotide sequences of the oligonucleotides having affinity to the CRPs.

```
                                          (SEQ ID NO: 7)
Forward primer F1 5'-ggcaggaagacaaaca-3'

(SEQ ID NO: 8)
Reverse primer R1 5'-acagcaccacagacca-3'
```

TABLE 1

| Reaction condition of PCR | |
| --- | --- |
| Contents of PCR reagent | Volume (μL) |
| Forward primer F1 (0.5 μM) | 1.5 |
| Reverse primer R1 (0.5 μM) | 1.5 |
| dNTPs (0.2 mM) | 2.4 |
| Super-Therm Gold DNA polymerase (1 U) | 0.2 |
| Reaction buffer (containing 1.5 mM $MgCl_2$) | 3 |

Deionized water is added to a total volume of 30 μL.
Operation condition: perform denaturing for 10 min at 94° C.; perform 20 cycles of: denaturing for 30 second (sec) at 94° C., primer annealing for 15 sec at 60° C., and elongation for 30 sec at 72° C.; finally stand for 7 min at 72° C.

Upon completion of the PCR reaction, the PCR product replicated according to each of the oligonucleotides having affinity to the CRPs is extracted with the pipette. After the integrated microfluidic chip system is cleaned with 75% ethanol, the PCR product extracted (3 μL), the bead solution A (17 μL), and 1% BSA solution (20 μL) are added to the reaction tank to repeat the PCR steps 4 times. Finally, the final product in the reaction tank is collected to perform the following experiment.

Experiment 2

Cloning of Aptamers Having Affinity to CRPs

The PCR product (1 μL) obtained from Experiment 1, pGEM®-T Easy vector (1 μL), 2× rapid ligation buffer (5 μL), and T4 DNA ligase (1 μL) are mixed well, and deionized water is added to make a total volume of the reaction to be 10 μL. The reaction is then placed on ice overnight. Afterwards, 50 μL of JM 109 *Escherichia coli* (*E. coli*) competent cells is added to the above solution and mixed well. The reaction is then placed on ice for 20 min. Next, the reaction undergoes heat shock for 45-50 sec in a 42° C. water bath and is rapidly transferred on ice for 2 min. Thereafter, 950 μL of SOC medium is added and incubated under 37° C. in a shaker for 1.5 hr at 150 revolution per min (rpm). The incubated product is well spread on an LB plate containing 1 mg/ML ampicillin, 0.5 mM isopropyl-β-D-thiogalactopyranoside (IPTG), and 80 μg/mL X-Gal, and incubated overnight at 37° C. Next, fifteen ampicillin-resistant colonies are picked from the LB plate and respectively inoculated into LB broth containing 1 mg/ML ampicillin. The inoculated cultures are then incubated at 37° C. for 16 hr. The fifteen cultures are sequenced respectively by Mission Biotech (Taiwan) to obtain the nucleotide sequences of the oligonucleotides having affinity to the CRPs.

Experiment 3

Screening of Aptamers Having Affinity to CRPs

Firstly, a 50 mg/L CRP solution and a 1% BSA solution are prepared respectively by dissolving human serum CRP and BSA in 0.05 M carbonate buffer. Next, 50 μL of the CRP solution obtained is added to a 0.2 mL PCR eppendorf and placed under 4° C. for coating overnight. The eppendorf with an inside wall coated with the CRPs is removed from 4° C. and washed with 0.01 M PBS for three times. Thereafter, 50 μL of 1% BSA solution is added and reacted under room temperature for 1 hr. Afterwards, the inside wall of the eppendorf is washed three times with 0.01 M PBS, and an eppendorf A with the inside wall coated with the CRPs is obtained for use.

In addition, 50 μL of the BSA solution obtained is added to a 0.2 mL PCR eppendorf and placed under 4° C. for coating overnight. The eppendorf with an inside wall coated with BSA is washed three times with 0.01 M phosphate buffer, and an eppendorf B with the inside wall coated with the BSA is obtained for use.

The fifteen PCR products obtained from Experiment 2 is randomly divided into five groups to form five groups of oligonucleotide mixtures (oligonucleotide mixtures 1-5). Here, each group of the oligonucleotide mixture includes three PCR products of equal volume being mixed well. Each group of the oligonucleotide mixture (oligonucleotide mixtures 1-5) then performs a following competitive test.

Here, 10 μL of the oligonucleotide mixtures 1-5 are respectively mixed well with 40 μL of 50 mg/L CRP solution. Subsequently, the reactant is incubated under 25° C. with a rotation of 200 rpm for 1 hr. Next, 50 μL of the reactant is added to the eppendorf A and incubated under 25° C. with a rotation of 200 rpm for 1 hr; this reactant is the experiment of each group. On the other hand, 10 μL of the oligonucleotide mixtures 1-5 are respectively mixed well with 40 μL of Tris buffer. The mixtures are added to the eppendorf A and the eppendorf B respectively to represent the positive control and negative control of each group. Moreover, a PCR eppendorf (with an inside wall uncoated with any substance) containing water is used as the blank control. All of the groups are incubated under 25° C. with a rotation of 200 rpm for 1 hr. Later, the reactants are washed three times with 0.01 M sodium phosphate buffer containing 0.5 M NaCl and 1% of Tween 20 (pH 7.4). A PCR reaction is then performed to the reactants with the pair of primers in Experiment 1 (including the forward primer F1 and the reverse primer R1) and referring to the reaction conditions listed in Table 1. The PCR products obtained therefrom are separated by performing an electrophoresis in a 8% agarose gel. The agarose gel is then stained with ethidium bromide and observed under ultraviolet light.

Figure 2:
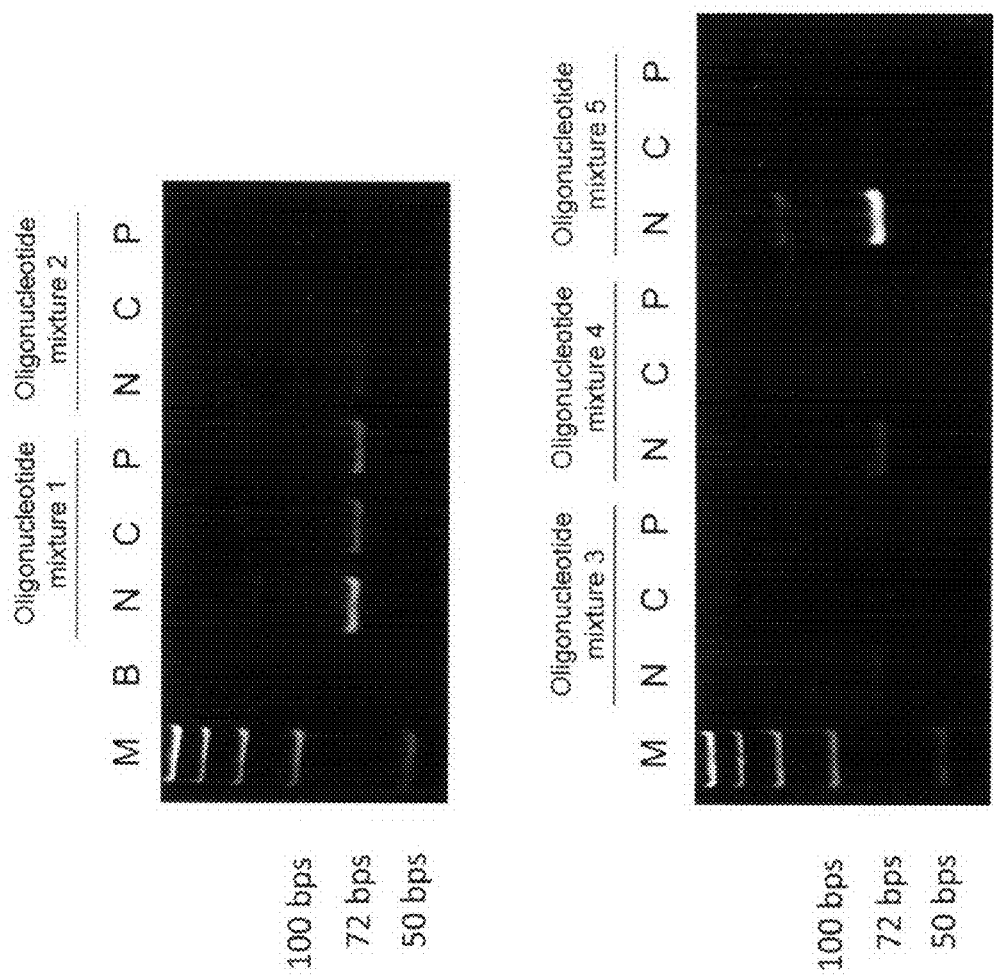
FIG. 2 illustrates a result of an agarose gel electrophoresis of polymerase chain reaction (PCR) products obtained from a PCR process performed using primers after oligonucleotide mixture 1-5 respectively undergo a competitive test. Here, M represents a deoxyribonucleic acid (DNA) ladder marker; B represents a blank; P represents a positive control; C represents an experiment; N represents a negative control.

Result:

FIG. 2 illustrates the result of the agarose gel electrophoresis of PCR products obtained from a PCR reaction performed using the primers after oligonucleotide mixture 1-5 respectively undergo the competitive test. Here, M represents a DNA ladder marker; B represents the blank; P represents the positive control; C represents the experiment; N represents the negative control. As shown in FIG. 2, in the oligonucleotide mixture 1, the negative control, the experiment, and the positive control each shows a band (with a size about 72 basepair (bp)) between 50 bp and 100 bp. Here, the band of the experiment is weaker than the band of the positive control. This depicts that in the pre-incubation, the three PCR products in the oligonucleotide mixture 1 did bind with the CRPs in the CRP solution to form CRP-PCR product complexes. Therefore, when the CRP-PCR product complexes formed in the pre-incubation are added to the eppendorf A, the CRPs already bound to the PCR products then compete with the CRPs coated on the inside wall of the eppendorf A. Furthermore, the band of the negative control may be caused by non-specific binding between the three PCR products in the oligonucleotide mixture 1 and the BSA in the eppendorf A due to insufficient washing. In the experimental results of the oligonucleotide mixtures 2-5, as the positive controls did not show bands or the bands thereof are weaker than those of the competitive test, the oligonucleotide mixtures 2-5 do not have specific binding ability to the CRPs. In other words, the experimental results show that the oligonucleotide mixture 1 includes aptamers having higher binding affinity to the CRPs.

Figure 3:
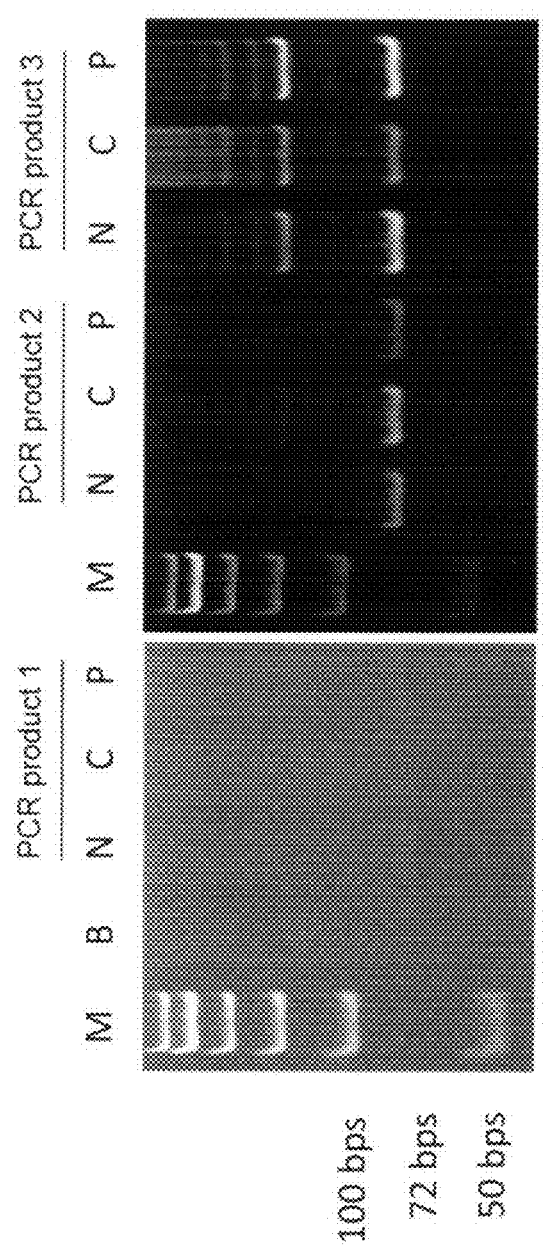
FIG. 3 illustrates a result of an agarose gel electrophoresis of PCR products obtained from a PCR process performed using primers after three PCR products, which are included in an oligonucleotide mixture 1, respectively undergo a competitive test. Here, M represents a DNA ladder marker; B represents a blank; P represents a positive control; C represents an experiment; N represents a negative control.

Then, the three PCR products in the oligonucleotide mixture 1 respectively undergo the competitive test to ensure which one(s) of the three PCR products includes aptamers having higher binding affinity to the CRPs. FIG. 3 illustrates the result of an agarose gel electrophoresis of PCR products obtained from a PCR reaction performed using the primers after three PCR products, which are included in the oligonucleotide mixture 1, respectively undergo the competitive test. Here, M represents the DNA ladder marker; B represents the blank; P represents the positive control; C represents the experiment; N represents the negative control. As shown in FIG. 3, the PCR product 1 and the PCR product 3 have higher affinity to the CRPs; thus, the PCR product 1 and the PCR product 3 are referred as aptamers A and aptamers B respectively. The aptamers A and the aptamers B are sequenced by Mission Biotech, and are respectively shown to include a following nucleotide sequence:

```
aptamer A:
                                         (SEQ ID NO: 4)
5'-ggcaggaagacaaacacgatgggggggtatgatttgatgtggttgt tgcatgatcgtggtctgtggtgctgt-3' aptamer B:
                                         (SEQ ID NO: 5)
5'-ggcaggaagacaaacacacaagcgggtgggtgtgtactattgcagt atctattctgtggtctgtggtgctgt-3'
```

By comparing the nucleotide sequences of the aptamer A and the aptamer B, Applicants conclude a central sequence of sixteen nucleotides to be essential for the binding affinity between the aptamers and the CRPs:

5'-angngggngnntgnnt-3' (SEQ ID NO: 1). Herein, n is a nucleotide selected from a, t, c, and g.

Experiment 4

Evaluation of Affinity of Aptamer to CRP

In the present experiment, the aptamers A screened out from Experiment 3 are analyzed with the SPR assay, so as to evaluate the affinity of the aptamers A to the CRPs from a dissociation constant $K_D$ of the CRP-aptamers obtained from the SPR assay. In particular, the present experiment evaluates the $K_D$ of the CRP-aptamers with a Biacore X system. Without additional illustration, the following experimental steps are all operated under 25° C. and a flow rate of 20 μL/min.

Firstly, the aptamers A undergo biotinylation by Medclub Scientific Co. Ltd. (Taoyuan, Taiwan), and the aptamers A with biotinylated 5' ends are obtained. The aptamers A are dissolved in deionized water to obtain an aptamer solution A with a concentration of 0.1 µM. Next, the aptamer solution A obtained is placed under 94° C. to be heated for 1 min. The aptamer solution A obtained is rapidly transferred to 4° C. for use. Additionally, the reverse primer R1 in Experiment 2 also undergoes the same biotinylation, and a suitable amount of biotinylated reverse primer R1 is dissolved in deionized water to obtain a reverse primer solution with a concentration of 0.1 µM.

Afterwards, a streptavidin-surface modified SA sensor chip is placed in the Biacore X system. Subsequently, 5×SSCT buffer (containing 750 mM NaCl, 75 mM sodium citrate, and 0.05% Tween 20, pH 7.0) is injected into the Biacore X system and passes the surface of SA sensor chip to wash the SA sensor chip. After the SPR response on the SA sensor chip reaches a balance, a washing buffer B containing 50 mM NaOH and 1M NaCl is used to wash the SA sensor chip 1 min for three times so as to activate the SA sensor chip. Next, a suitable amount of 5×SSCT buffer is applied to wash the SA sensor chip until the SPR response reaches a balance again.

Then, 90 µL of the aptamer solution A being cooled to 4° C. is aliquoted, and the aptamer solution A is injected to pass the surface of the SA sensor chip, so that the aptamers A in the aptamer solution A is coated on the surface of the SA sensor chip. Later, 90 µL of the reverse primer solution is injected and passes through the surface of the SA sensor chip for blocking. Subsequently, 5×SSCT buffer is used to wash the surface of the SA sensor chip until the SPR response reaches a balance.

Five cycles as described in the following are then performed. Here, each cycle includes: (1) injecting 90 µL of the testing solution to pass through the surface of the SA sensor chip; (2) washing the surface of the SA sensor chip by using 90 µL of a washing buffer C (10 mM Tris buffer containing 50 mM NaCl and 2 mM $CaCl_2$); (3) recording the SPR response of the SA sensor chip for 5 min; and (4) injecting 90 µL of 100 mM NaOH to pass the surface of the SA sensor chip, so that the surface of the SA sensor chip is regenerated. The testing solutions used in the five cycles are washing buffers C respectively having a CRP concentration of 0.01, 0.05, 0.1, and 0.5 mg/L.

The SPR response measured by the Biacore X system is a function of the resonance angle change (represented by arbitrary units, a.u.), where a graph is plotted using the SPR response measured by the Biacore X system and the corresponding time. Also, a BIA evaluation program (version 3.2, GE Healthcare) is also used to substitute the SPR response measured by the Biacore X system into a Langmuir binding model having a 1:1 stoichiometry to calculate an association rate constant ($k_{on}$, shown in $M^{-1}s^{-1}$) and a dissociation rate constant ($k_{off}$, shown in $s^{-1}$) of the CRP-aptamer A. Moreover, $K_D$ of the CRP-aptamer A is determined by a ratio of $k_{off}$ to $k_{on}$.

Figure 4:
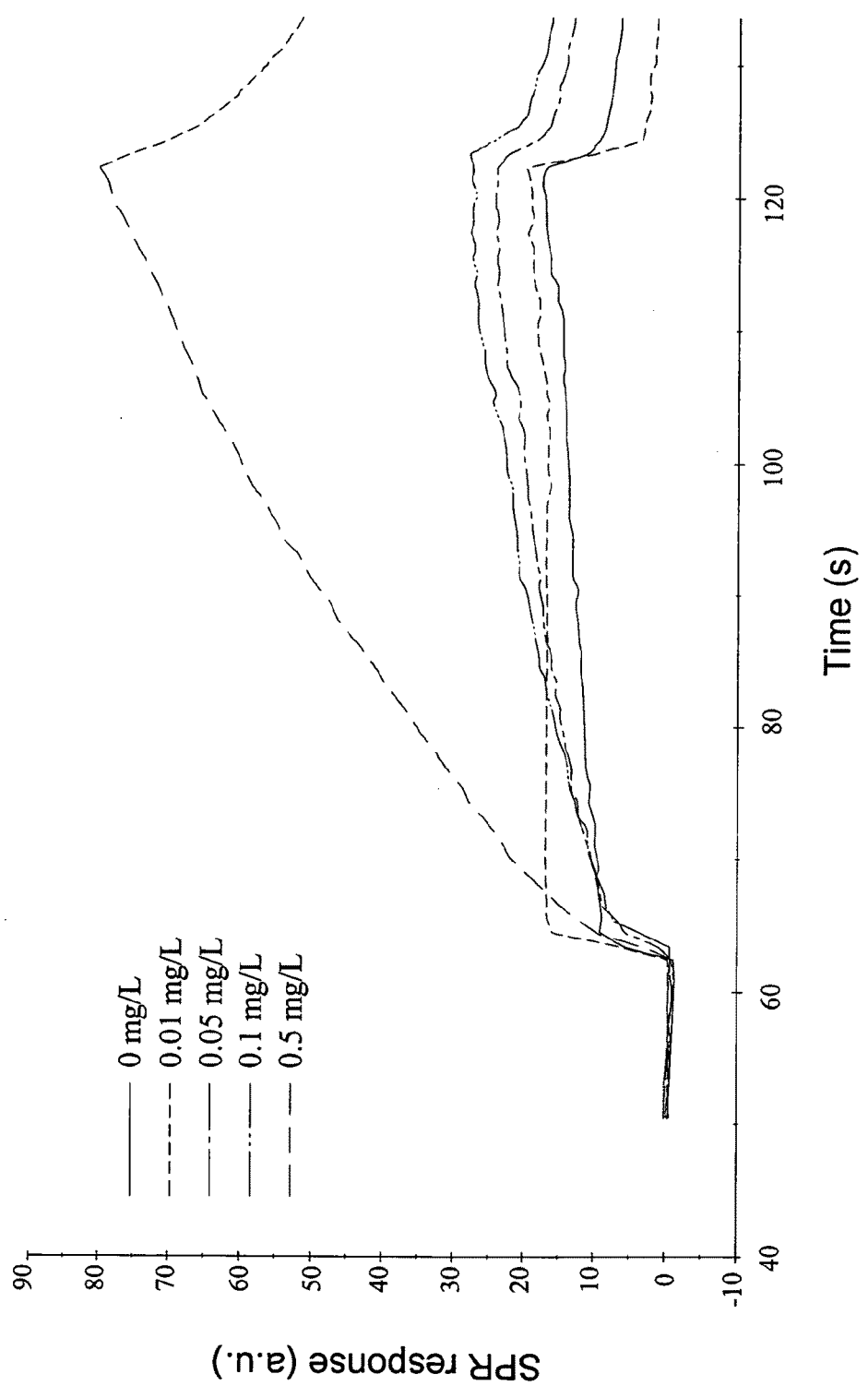
FIG. 4 is a surface plasmon resonance (SPR) response measured under different CRP concentrations detected by an SA sensor chip coated with aptamers A along with time in a Biacore X system.

Result:

FIG. 4 is a SPR response measured under different CRP concentrations detected by the SA sensor chip coated with aptamers A along with time in the Biacore X system. As depicted in FIG. 4, the binding between the aptamers A and the CRPs increases with the increase in CRP concentration. Particularly, when the CRP concentration is 0.5 mg/L, the binding effect between the CRPs and the aptamers A increases significantly with time, which shows the strong binding affinity of the aptamers A to the CRPs. Further, the results of the SPR response measured are substituted into the Langmuir binding model to obtained $K_D$ of the CRP-aptamer A. The $K_D$ of the CRP-aptamer A obtained is 3.51 nM; this represents the high affinity between the aptamers A and the CRPs.

Experiment 5

Detection Method for CRP Adopting Aptamer A

1. Fabrication of Aptamer A-Conjugated Beads

Firstly, 500 µL of E170 streptavidin-coated beads is extracted with the pipette to two eppendorfs respectively. The eppendorfs are placed in a magnet, so that the E170 streptavidin-coated beads are attracted to the magnet so as to move toward the magnet and adsorb to inside walls of the eppendorfs. Residues in the eppendorfs not attracted by the magnetic field are removed. The beads are then washed three times with 500 µL of 5×SSCT solution (750 mM NaCl, 75 mM sodium citrate, 0.05% Tween 20, pH 7.0).

Next, 5 µL of cooled biotinylated aptamers A (10 µM) after heating and 495 µL of 5×SSCT solution are added into the eppendorf and mixed well. Afterwards, the eppendorf is removed from the magnet and placed under room temperature for 1 hr, such that the biotinylated aptamers A are conjugated to the E170 streptavidin-coated beads to form aptamer A-conjugated beads (referred as beads B).

Thereafter, the eppendorf is removed and placed inside the magnet, and the beads B are adsorbed to the inside wall of the eppendorf. Residues in the eppendorf that are not attracted by the magnetic field are removed and the beads B are washed three times with 500 µL of 2×SSCT. The eppendorf is then removed from the magnet and placed under 4° C. for blocking overnight with 1000 µL Tris buffer (containing 1% BSA).

2. Immunoassay of Aptamer A

Firstly, 10 µL of a serum sample to be tested (with a CRP concentration of 1.41 mg/L measured by Department of Pathology of National Cheng Kung University Hospital) and 190 µL of the beads B are added to an eppendorf. The reactant is then mixed on an orbital shaker (1,200 rpm) for 120 min under room temperature, such that the beads B having the biotinylated aptamers A bind with the CRPs in the serum sample. Thereafter, the eppendorf is placed in the magnet for the beads B to adsorb on an inside wall of the eppendorf. Subsequently, the beads B are washed three times with a buffer D (0.01 M sodium phosphate buffer containing 0.5 M NaCl and 0.1% Tween, pH 7.4).

Then, anti-CRP antibodies (200 µL) labeled with acridinium C2NHS ester is added to the eppendorf and mixed on the orbital shaker (1,200 rpm) for 60 min under room temperature. The eppendorf is placed in the magnet, so that the beads B adsorb to the inside wall of the eppendorf. The beads B are then washed three times with the washing buffer D. Next, 200 µL of nitric acid (containing 0.6% $H_2O_2$) is added and mixed well, and 100 µL of 0.75 N sodium hydroxide (containing 1.5% Triton X-100) is subsequently added. Thereafter, an AutoLumat LB 953 photometer is used to measure relative fluorescent unit (RLU). The above experiment is repeated three times.

On the other hand, RLU of the CRP standard solutions with known concentrations (0.0125, 0.0625, 0.125, 0.625, 2.5, and 10 mg/L) is measured, and a graph is plotted with Log values (Log mg/L) of the concentrations of the CRP standard solutions versus Log values (Log RLU) of corresponding RLU to obtain a standard curve. The standard curve is then applied to convert the CRP concentration (mg/L) of the serum sample to be tested using the RLU of the serum sample to be tested.

Figure 5:
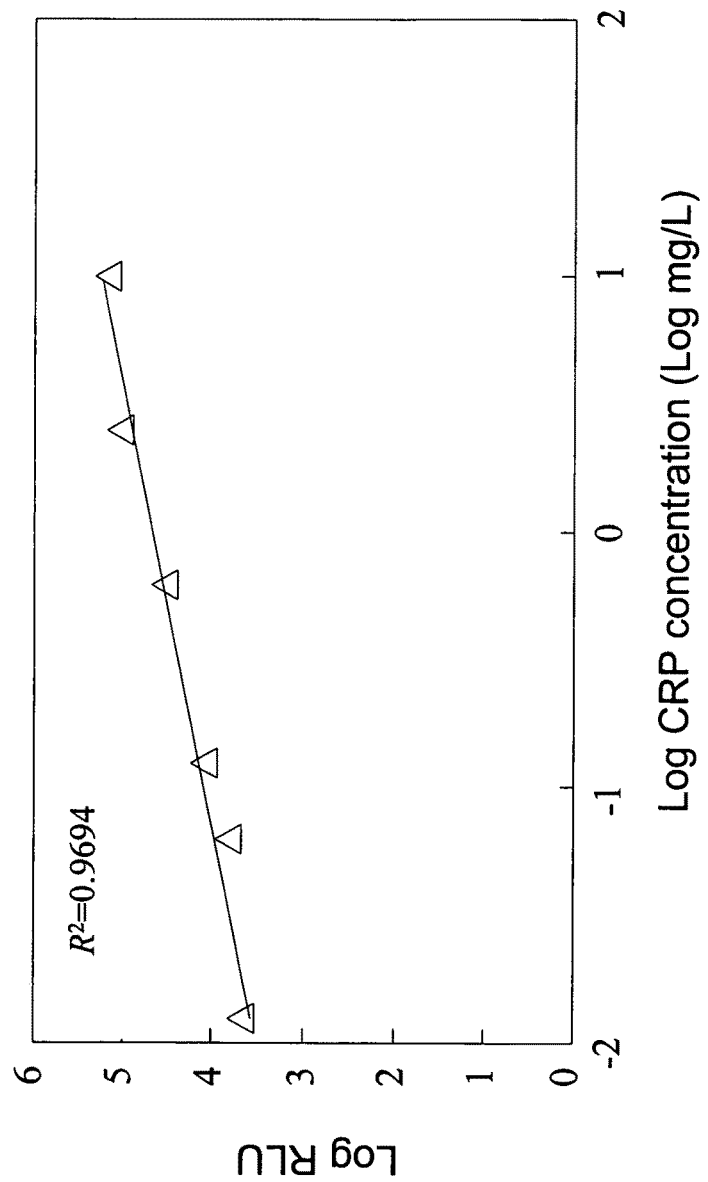
FIG. 5 depicts a standard curve obtained from Log values (Log mg/L) of concentrations of CRP standard solutions having known concentrations (0.0125, 0.0625, 0.125, 0.625, 2.5, and 1 mg/L) versus Log values (Log RLU) of corresponding relative fluorescent units.

Result:

FIG. 5 depicts the standard curve obtained from Log values of concentrations of the CRP standard solutions having known concentrations (0.0125, 0.0625, 0.125, 0.625, 2.5, and 1 mg/L) versus Log values (Log RLU) of corresponding RLU. According to the standard curve: a linear relationship of the Log values of the concentrations of the CRP standard solutions relative to the Log values of the RLUs falls within a range from 0.0125 mg/L to 10 mg/L ($R^2$=0.9694), and a detecting limit of the aptamers A to the concentration of the CRPs is 0.0125 mg/L.

The following equation can be deduced from the standard curve.

$$Y=0.4484X+4.591, \text{ where } X \text{ is the Log value of RLU and } Y \text{ is the Log value of CRP concentration.}$$

The Log value of the CRP concentration of the serum sample can be acquired by substituting the RLU measured from the serum sample into the above equation. Then, the Log value of the CRP concentration obtained is inversely operated to acquire the CRP concentration of the serum sample. The CRP concentrations obtained from the three experiments are averaged to acquire an average CRP concentration of the serum sample to be 1.85 mg/L. This value is close to the value (1.41 mg/L) measured by the Department of Pathology of National Cheng Kung University Hospital. The experiment result shows: the detecting limit of the CRP detection method adopting the aptamers A can reach 0.0125 mg/L and the method has high sensitivity to the CRPs. Moreover, the CRP detection method adopting the aptamers A has high reliability. Thus, the CRP detection method adopting the aptamers A is suitable for qualitative and quantitative analysis of CRP in clinical serum samples.

In summary, the aptamers of the invention specifically bind to the CRPs and have high affinity to the CRPs. Therefore, the aptamers of the invention can be widely applied in the detection method for the CRPs and biotechnologies such as CRP target drugs. In particular, since the aptamers of the invention have simple fabrication, low cost, minimal batch difference and storage stability, the detection method for the CRPs adopting the aptamers has high sensitivity, high stability, and high accuracy, and can be used in clinical examination and academic research for assessment and prevention of disease.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An aptamer specifically binding to a C-reactive protein and comprising a following nucleotide sequence:

(SEQ ID NO: 4)
5'-ggcaggaagacaaacacgatgggggggtatgatttgatgtggttgtt gcatgatcgtggtctgtggtgctgt-3'.

2. The aptamer as claimed in claim 1, wherein a binding affinity (Kd) between the aptamer and the C-reactive protein ranges from 0.3 nanomole (nM) to 30 nM.

3. The aptamer as claimed in claim 1, having a 5' end modified by a thiol group, a biotin, a fluorescent label, or an enzyme.

4. The aptamer as claimed in claim 1, comprising 72 to 80 nucleotides.

5. A detection method for a C-reactive protein, adapted for detecting the C-reactive protein in a sample, the detection method comprising: providing the aptamer as claimed in claim 1; mixing the sample and the aptamer, such that the C-reactive protein in the sample and the aptamer bind to form a C-reactive protein-aptamer; anddetecting the C-reactive protein or the aptamer in the C-reactive protein-aptamer.

6. The detection method for the C-reactive protein as claimed in claim 5, wherein the aptamer is labeled with a fluorescent label or a luminescent label.

7. A detection method for a C-reactive protein, adapted for detecting the C-reactive protein in a sample, the detection method comprising: providing a plurality of beads non-covalently bonded to the aptamer as claimed in claim 1 respectively; mixing the beads and the sample, such that the aptamers on the beads bind with the C-reactive proteins in the sample; adding C-reactive protein antibodies to the sample mixed with the beads, such that the C-reactive protein antibodies bind with the C-reactive proteins bound on the beads;
removing the unbound C-reactive protein antibodies; and
detecting the C-reactive protein antibodies bound to the beads through the C-reactive proteins.

8. The detection method for the C-reactive protein as claimed in claim 7, wherein the aptamer and the bead are non-covalently bonded through a biotin-streptavidin interaction.

* * * * *

SEQUENCE LISTING

```
<160> NUMBER OF SEQ ID NOS: 8

<210> SEQ ID NO 1
<211> LENGTH: 16
<212> TYPE: DNA
<213> ORGANISM: Artificial Sequence
<220> FEATURE:
<223> OTHER INFORMATION: aptamer, specifically binding to C-reactive
      protein
<220> FEATURE:
<221> NAME/KEY: misc_feature
<222> LOCATION: (2)..(2)
<223> OTHER INFORMATION: n =a, g, c or t
<220> FEATURE:
<221> NAME/KEY: misc_feature
<222> LOCATION: (4)..(4)
<223> OTHER INFORMATION: n =a, g, c or t
<220> FEATURE:
<221> NAME/KEY: misc_feature
<222> LOCATION: (8)..(8)
<223> OTHER INFORMATION: n =a, g, c or t
<220> FEATURE:
<221> NAME/KEY: misc_feature
<222> LOCATION: (10)..(11)
<223> OTHER INFORMATION: n =a, g, c or t
<220> FEATURE:
<221> NAME/KEY: misc_feature
<222> LOCATION: (14)..(15)
<223> OTHER INFORMATION: n =a, g, c or t

<400> SEQUENCE: 1 angnggngn ntgnnt                                                  16

<210> SEQ ID NO 2
<211> LENGTH: 16
<212> TYPE: DNA
<213> ORGANISM: Artificial Sequence
<220> FEATURE:
<223> OTHER INFORMATION: aptamer ,specifically binding to C-reactive
      protein

<400> SEQUENCE: 2
```

```
atgggggggt atgatt                                                         16

<210> SEQ ID NO 3
<211> LENGTH: 16
<212> TYPE: DNA
<213> ORGANISM: Artificial Sequence
<220> FEATURE:
<223> OTHER INFORMATION: aptamer ,specifically binding to C-reactive
      protein

<400> SEQUENCE: 3
aagcgggtgg gtgtgt                                                         16

<210> SEQ ID NO 4
<211> LENGTH: 72
<212> TYPE: DNA
<213> ORGANISM: Artificial Sequence
<220> FEATURE:
<223> OTHER INFORMATION: aptamer A

<400> SEQUENCE: 4
ggcaggaaga caaacacgat gggggggtat gatttgatgt ggttgttgca tgatcgtggt         60
ctgtggtgct gt                                                             72

<210> SEQ ID NO 5
<211> LENGTH: 72
<212> TYPE: DNA
<213> ORGANISM: Artificial Sequence
<220> FEATURE:
<223> OTHER INFORMATION: aptamer B

<400> SEQUENCE: 5
ggcaggaaga caaacacaca agcgggtggg tgtgtactat tgcagtatct attctgtggt         60
ctgtggtgct gt                                                             72

<210> SEQ ID NO 6
<211> LENGTH: 72
<212> TYPE: DNA
<213> ORGANISM: Artificial Sequence
<220> FEATURE:
<223> OTHER INFORMATION: oligonucleotides of oligonucleotide library
<220> FEATURE:
<221> NAME/KEY: primer_bind
<222> LOCATION: (1)..(16)
<220> FEATURE:
<221> NAME/KEY: misc_feature
<222> LOCATION: (17)..(56)
<223> OTHER INFORMATION: n is a, c, g, or t
<220> FEATURE:
<221> NAME/KEY: primer_bind
<222> LOCATION: (57)..(72)

<400> SEQUENCE: 6
ggcaggaaga caaacannnn nnnnnnnnnn nnnnnnnnnn nnnnnnnnnn nnnnnntggt         60
ctgtggtgct gt                                                             72

<210> SEQ ID NO 7
<211> LENGTH: 16
<212> TYPE: DNA
<213> ORGANISM: Artificial Sequence
<220> FEATURE:
<223> OTHER INFORMATION: forward primer F1

<400> SEQUENCE: 7
ggcaggaaga caaaca                                                         16
```

```
<210> SEQ ID NO 8
<211> LENGTH: 16
<212> TYPE: DNA
<213> ORGANISM: Artificial Sequence
<220> FEATURE:
<223> OTHER INFORMATION: reverse primer R1

<400> SEQUENCE: 8
acagcaccac agacca                                                    16
```